(12) United States Patent
Mault

(10) Patent No.: US 6,610,012 B2
(45) Date of Patent: Aug. 26, 2003

(54) SYSTEM AND METHOD FOR REMOTE PREGNANCY MONITORING

(75) Inventor: James R. Mault, Evergreen, CO (US)

(73) Assignee: Healthetech, Inc., Golden, CO (US)

( * ) Notice: Subject to any disclaimer, the term of this patent is extended or adjusted under 35 U.S.C. 154(b) by 329 days.

(21) Appl. No.: 09/829,901

(22) Filed: Apr. 10, 2001

(65) Prior Publication Data

US 2002/0028995 A1 Mar. 7, 2002

Related U.S. Application Data

(60) Provisional application No. 60/195,779, filed on Apr. 10, 2000, provisional application No. 60/206,905, filed on May 25, 2000, and provisional application No. 60/225,454, filed on Aug. 15, 2000.

(51) Int. Cl.[7] .............................................. A61B 8/00
(52) U.S. Cl. ........................ 600/437; 600/300; 600/382
(58) Field of Search ................................ 600/300, 301, 600/304, 313, 338, 351, 376, 382, 386, 390, 391, 437, 442, 448, 453, 459, 511, 551, 586, 587; 128/903, 916

(56) References Cited

U.S. PATENT DOCUMENTS

| | | | |
|---|---|---|---|
| 5,042,499 A | * 8/1991 | Frank et al. ................ | 600/511 |
| 5,438,996 A | 8/1995 | Kemper et al. ............. | 600/448 |
| 5,713,371 A | 2/1998 | Sherman et al. ............ | 600/436 |
| 5,851,188 A | * 12/1998 | Bullard et al. .............. | 600/448 |
| 6,024,701 A | * 2/2000 | Almog ........................ | 600/300 |
| 6,045,500 A | * 4/2000 | Bieniarz ..................... | 600/300 |
| 6,340,346 B1 | * 1/2002 | Almog et al. ............... | 600/300 |
| 6,364,844 B1 | * 4/2002 | Regas et al. ................ | 600/551 |

* cited by examiner

*Primary Examiner*—Willis R. Wolfe
(74) *Attorney, Agent, or Firm*—Gifford, Krass, Groh, Sprinkle, Anderson & Citkowski, P.C.

(57) ABSTRACT

A system and method for remote pregnancy monitoring of a pregnant woman is provided. The system includes an ultrasound transducer positioned on a pregnant woman having a processor, a transmitter and a receiver, and a personal digital assistant operatively connected to the ultrasound transducer via a communication link. The system also includes a patient computer system operatively connected to the personal digital assistant via a second communication link. The system further includes a healthcare provider computer system operatively connected to the patient computer system via an internet, and activation of the ultrasound transducer generates a data signal transmitted to the personal digital assistant via the communication link, and transmission of the signal to the healthcare provider computer system via the second communication link, for monitoring the pregnant woman by a healthcare provider.

21 Claims, 4 Drawing Sheets

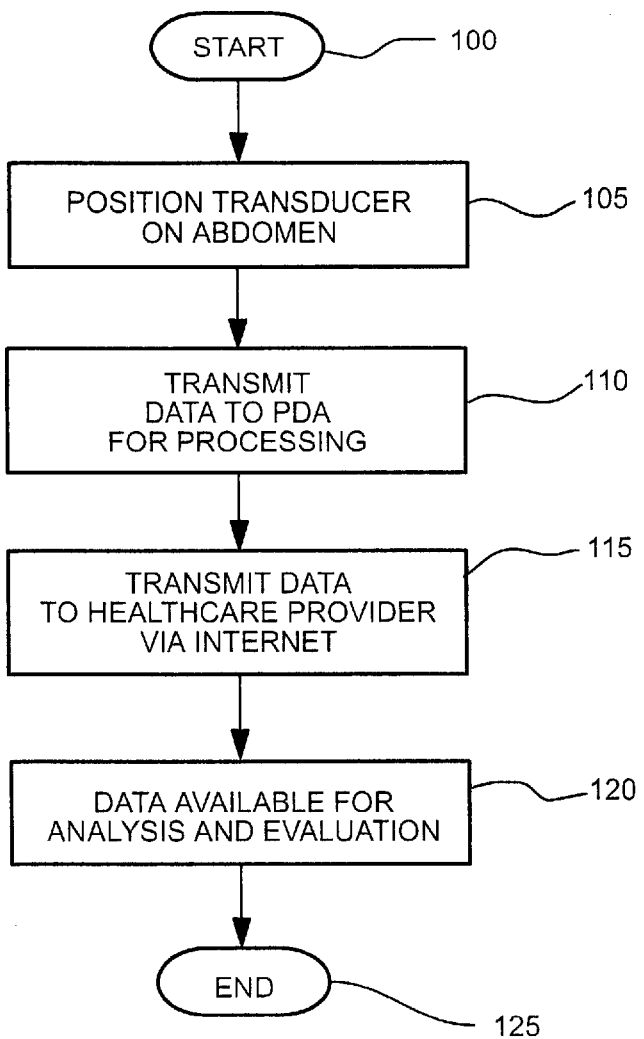
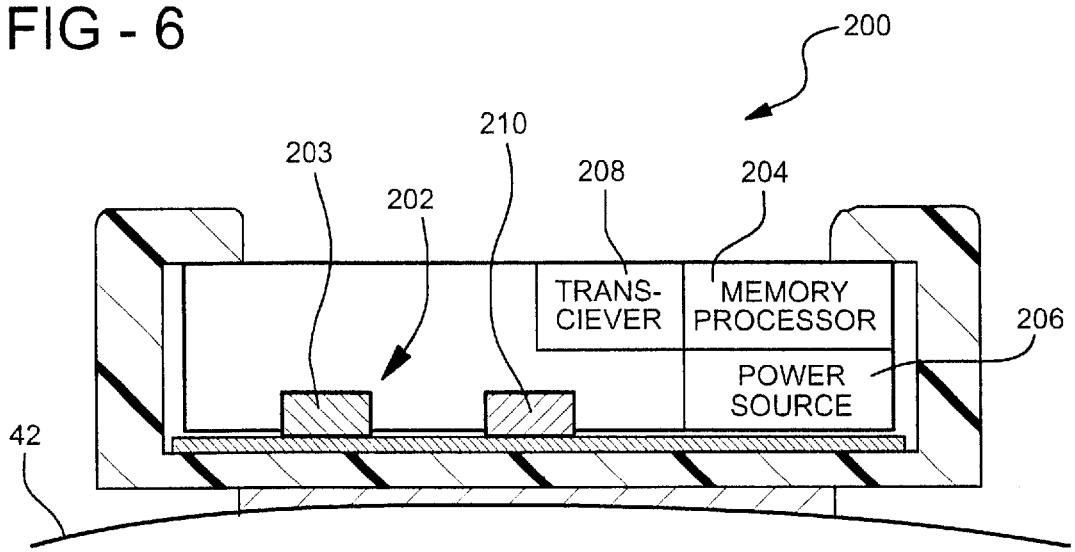

SYSTEM AND METHOD FOR REMOTE PREGNANCY MONITORING

REFERENCE TO RELATED APPLICATION

This application claims priority of U.S. Provisional Patent Application Ser. Nos. 60/195,779 (filed Apr. 10, 2000), 60/206,905 (filed May 25, 2000), and 60/225,454 (filed Aug. 15, 2000), the entire contents of all of which are incorporated herein by reference.

BACKGROUND OF THE INVENTION

1. Field of the Invention

The present invention relates generally to medical monitoring, more specifically, to a system and method for remote monitoring of a pregnancy-related physiological condition in a pregnant female patient.

2. Description of the Related Art

Medical monitoring involves the measurement of a physiological condition of a patient. An example of a medical monitor is disclosed in U.S. application Ser. Nos. 09/669,125 (filed Sep. 25, 2000) and 09/821,417 (filed Mar. 29, 2001, "Monitoring System"), the disclosures of which are incorporated herein by reference. With certain medical conditions, it is advantageous from a health and cost perspective to conduct this type of monitoring within a home-based setting. For example, a pregnant female patient may require periodic evaluation of uterine activity for pre-term labor management by a healthcare provider. In the past, the patient was taught to time her uterine contractions, and report her results to the healthcare provider. However, this method is not very accurate, since it relies on the patient to accurately perceive uterine activity. Alternatively, the patient was monitored either in her home or at the doctor's office using an electronic uterine monitoring system. Monitoring the patient at the doctor's office requires frequent visits to the doctor's office, which is time consuming and may contradict prophylactic bed rest for a high risk patient.

Home monitoring involves the use of a home uterine activity monitor, which includes a transducer operatively connected to a data recorder, which is operatively connected via a phone line to a healthcare provider. Activation of the transducer produces a signal that is transmitted via the phone lines to the healthcare provider for evaluation. The signal may be sent directly to the healthcare provider, or to a home healthcare management service, for data analysis and evaluation.

While these types of pregnancy monitors work, they utilize a dedicated data recorder and transmitting device. Thus, there is a need in the art for a remote pregnancy monitor that measures a physiological condition of the pregnant female patient, including her in-utero fetus, and collects the data on a personal digital assistant and transmits the collected data via the Internet for analysis and evaluation purposes.

SUMMARY OF THE INVENTION

Accordingly, the present invention is a system and method for remote monitoring of a pregnant woman. The system includes an ultrasound transducer positioned on a pregnant woman having a processor, a transmitter and a receiver, and a personal digital assistant operatively connected to the ultrasound transducer via a communication link. The system also includes a patient computer system operatively connected to the personal digital assistant via a second communication link. The system further includes a healthcare provider computer system operatively connected to the patient computer system via an internet, and activation of the ultrasound transducer generates a data signal transmitted to the personal digital assistant via the communication link, and transmission of the signal to the healthcare provider computer system via the second communication link, for monitoring the pregnant woman by a healthcare provider. The method includes the steps of positioning the ultrasound transducer on the pregnant female in a predetermined location to monitor a predetermined condition and activating the ultrasound transducer to generate a signal for monitoring the predetermine condition. The method also includes the steps of transmitting the signal from the ultrasound transducer to the personal digital assistant, and transmitting the signal for monitoring the predetermined condition via an internet to a healthcare provider computer. The method further includes the steps of using the signal to remotely monitor the pregnant woman.

One advantage of the present invention is that a system and method for remote pregnancy monitoring is provided that measures a physiological condition of the pregnant female patient, stores the data, and transmits the data regarding the pregnancy to a healthcare provider via the Internet. Another advantage of the present invention is that the system and method includes an ultrasound transducer that measures the physiological condition of the pregnant woman. Still another advantage of the present invention is that the system and method includes a personal digital assistant that stores the measured data and transmits the data via the Internet to the healthcare provider. A further advantage of the present invention is that the healthcare provider can evaluate the condition of the pregnant woman in real-time, irrespective of their physical locations.

Other features and advantages of the present invention will be readily appreciated, as the same becomes better understood after reading the subsequent description taken in conjunction with the accompanying drawings.

BRIEF DESCRIPTION OF THE DRAWINGS

FIG. 3 is a flowchart of a method for remote pregnancy monitoring, according to the present invention, utilizing the system of FIG. 1.

FIG. 6 is a diagrammatic view of a further embodiment of a unitary monitoring mechanism, for use with a remote pregnancy monitor, according to the present invention.

DESCRIPTION OF THE PREFERRED EMBODIMENT(S)

Figure 1:
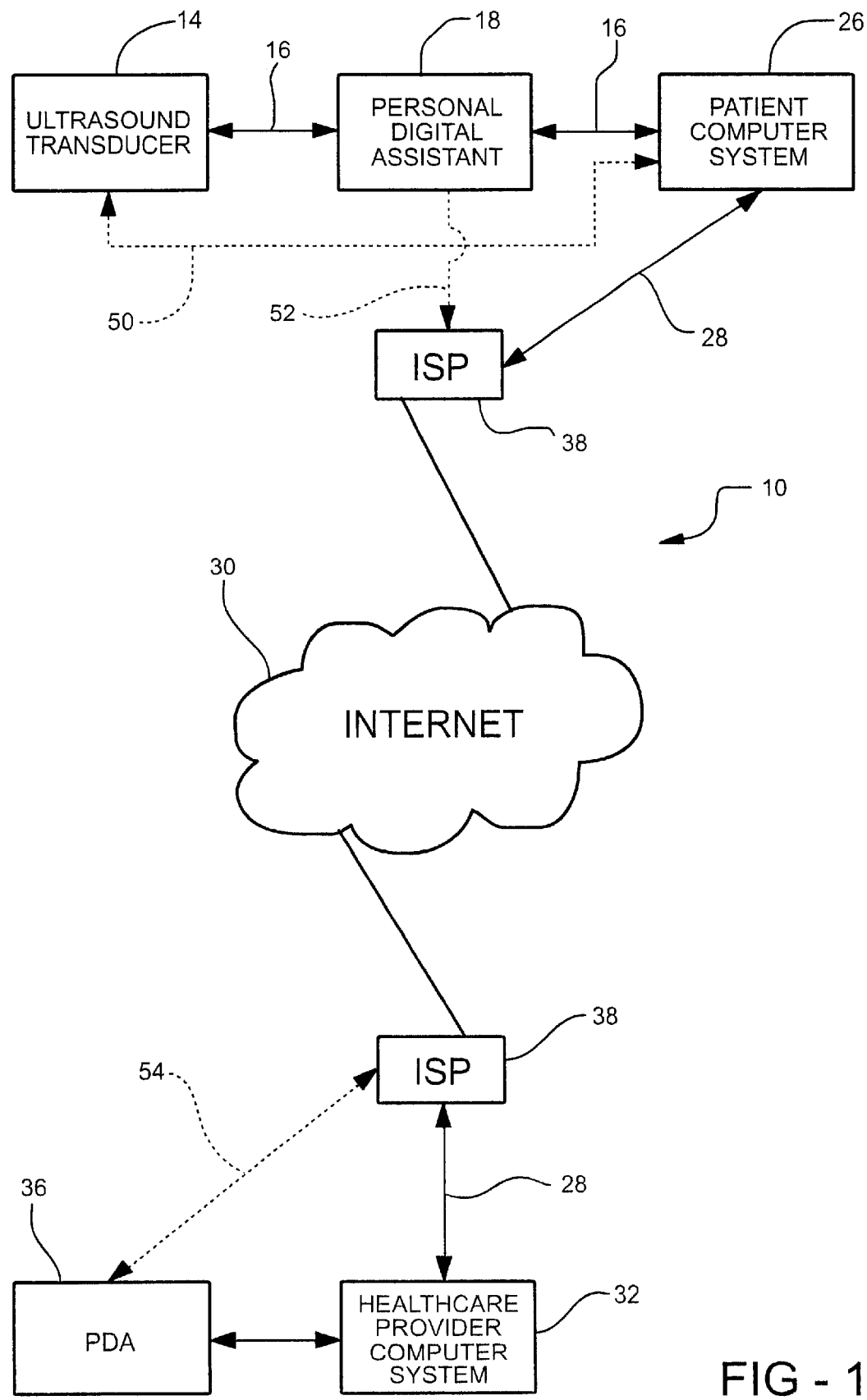
FIG. 1 is a schematic diagram of a system for remote pregnancy monitoring, according to the present invention.
Figure 2:
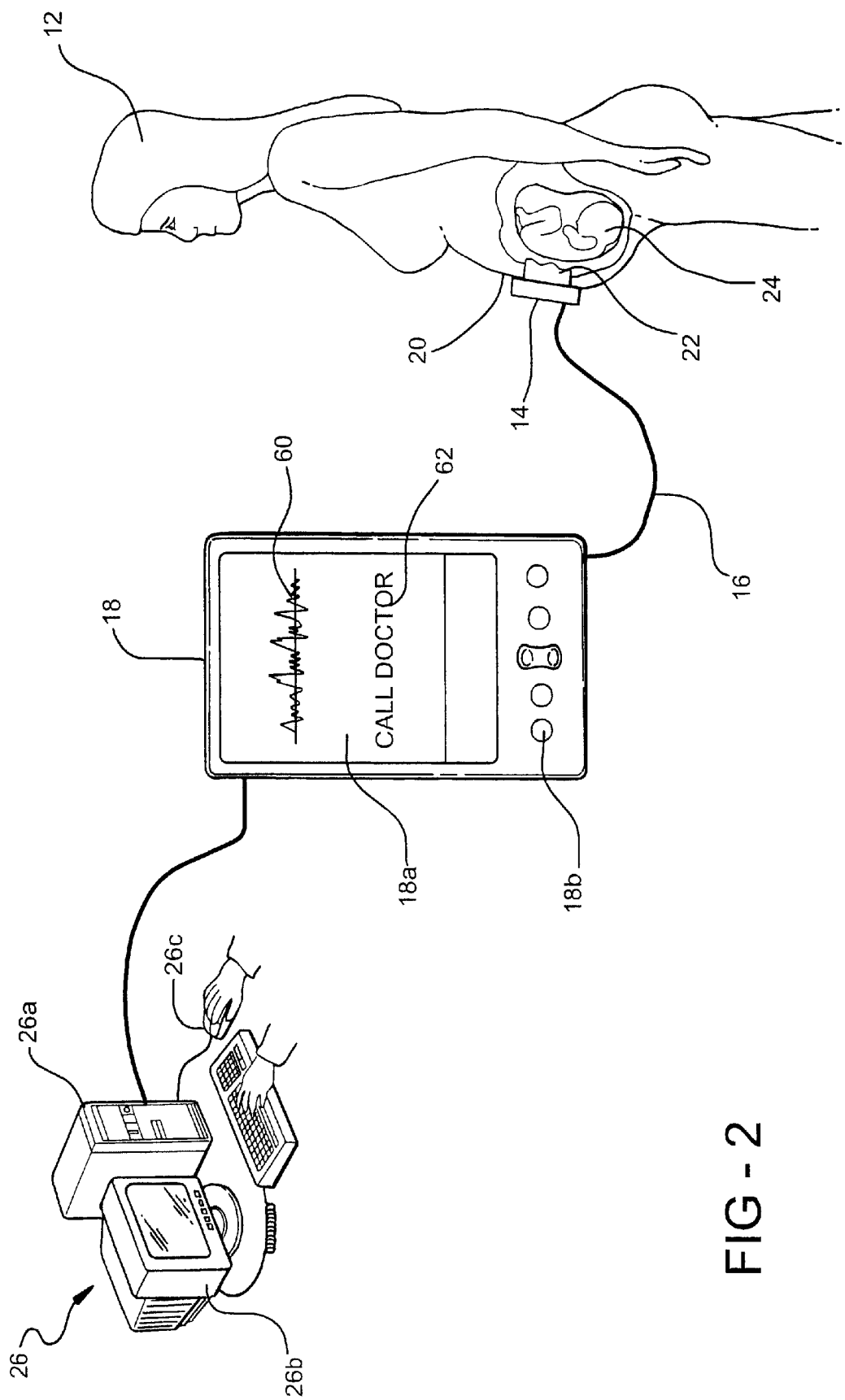
FIG. 2 is a side view of a pregnant woman using the system of FIG. 1, according to the present invention.

Referring to FIGS. 1 and 2, a system 10 for remote pregnancy monitoring of a pregnant woman 12 is illustrated. The system 10 includes an ultrasound transducer 14 having a processor, a transmitter, and a receiver. The ultrasound transducer 14 generates a signal, encapsulates the measurement data therein, and transmits the signal via a telecommunication link 16 to a personal digital assistant 18 in a manner to be described. Preferably, the ultrasound transducer 14 is attached to an external surface of the mother's abdomen 20, such as by a belt 22. Once attached, the mother 12 activates the ultrasound transducer 14, which generates an ultrasonic signal targeted at a predetermined fixed point, such as the symphysis pubis or coccyx of the mother 12. The ultrasonic signal bounces from the predetermined fixed point to the transducer 14, wherein the transducer 14 receives the ultrasonic signal. The processor portion of the ultrasound transducer 14 calculates the distance of the ultrasonic path measured between the predetermined fixed point and the ultrasound transducer 14.

An example of an ultrasound transducer 14 is a silicon-based ultrasonic transducer manufactured by Sensant. The ultrasonic transducer includes a microscopic transducer formed on a silicon wafer using an etching technique. A plurality of microscopic transducers may be arranged in an array, to enhance the real-time imaging capability of the ultrasonic transducer.

Alternatively, the ultrasound transducer 14 includes two sensors attached to predetermined points on the external abdominal or lumbar regions of the woman 12, and the path therebetween the sensor is measured. It should be appreciated that the ultrasound transducer 14 may further be attached to the external thoracic region of the in-utero fetus shown at 24 to collect and transmit various data regarding the fetus 24, such as respiration and heart rates.

The system 10 includes a personal digital assistant (PDA) 18 having a memory, a processor, a display screen 18a and an input mechanism 18b that operatively receives the signal transmitted by the ultrasound transducer 14, processes the signal, and transmits the signal in a manner to be described. The PDA 18 includes all portable computing devices, such as a notebook computer, a hand-held computer, a palm-held organizer, a web-enabled cellular phone, or the like that provides computing and information storage and retrieval. In this example, the PDA 18 is a hand-held device, such as the PALM or HANDSPRING VISOR. It should be appreciated that in an alternative embodiment, a personal computer 24 (to be described) is used to receive, process and transmit the signal from the ultrasound transducer 14, as shown at 50.

The system 10 also includes a telecommunication link 16 for communicating between the ultrasound transducer 14 and the PDA 18. The telecommunication link 16 can be a wire operatively connecting the PDA and ultrasound transducer. Alternatively, the telecommunication link is a wireless link. One example of a wireless link is a universal shortwave wireless connectivity protocol referred to as BLUETOOTH, as is known in the art. Another example of a wireless link is a memory module, also known as a memory stick. The ultrasound transducer 14 transmits continuously, at predetermined intervals based on a time unit contained therein, or at such a time as remotely triggered by a signal transmitted from the PDA 18.

The system 10 includes a patient computer system 26 operatively connected to the PDA 18, for receiving information from the PDA 18 and transmitting the information via a communication link 28 over the internet 30, to a healthcare provider computer system 32. The patient and healthcare provider computer systems 26, 32 are connected to an internet infrastructure 30, such as the Internet, via a telecommunication link 34, such as wires (e.g. a telephone line or a cable line) or a wireless connection. It should be appreciated that the patient computer system 26 and healthcare provider computer system 32 are conventional and known in the art. The patient computer system 26 includes a process and memory 26a, display terminal 26b, and input device 26c.

In an alternative embodiment shown at 52, the PDA 18 is a wireless PDA capable of directly accessing the internet 30 using wireless technology, as is known in the art. It should be appreciated that the healthcare provider may access the patient information on the healthcare provider computer system 32. Alternatively, the healthcare provider can access the information via a PDA 36, as shown at 54.

As is known in the art, the Internet 30 includes providers, such as Internet Access Providers (IAPs), Internet Service Providers (ISPs) and Network Service Providers (NSPs) (not shown) and routers (not shown) that provide wired and wireless digital telecommunications throughout the world using a TCP/IP networking protocol. It should be appreciated that the computers 26, 32 or PDAs 18, 36 may access the Internet directly, or they may be operatively connected to a Local Area Network (LAN) (not shown) over which information is transmitted to other computers on the same LAN or to computers on other LANS through a localized Intranet.

The Internet 30 includes a plurality of web site servers (not shown) that interactively transfer information to a user through the user's computer. The web site server is a computer system operatively connected to a provider in a conventional manner. The web site provides for interactive communication between the host of the web site and a visitor to the web site. The communication is facilitated by a series of screens, referred to as pages, displayed on the display screen, with the first page referred to as a home page. When the user visits a particular web site, the user is served a page displayed on the video monitor referred to as a home page. The user may interact with the page via the input device, such as by making a selection or a request.

Referring to FIG. 3, a method for remote pregnancy monitoring is provided. The method begins in bubble 100 and continues to block 105, with the woman 12 positioning the ultrasound transducer 14 on her abdomen 20. The methodology advances to block 105. In block 105, a predetermined condition such as uterine contractions, are measured. For example, the woman 12 activates the ultrasound transducer 14, which generates a real-time three-dimensional image of the fetus 24, as previously described. The methodology advances to block 110.

In block 110, the data from the ultrasound transducer 14 is transmitted to the PDA 18 for processing. The PDA 18 receives the data from the ultrasound transducer 14 and generates a set of values and interpretive information from the data. The data is stored on the PDA 18. For example, the PDA 18 receives the data as a set of ultrasonic path measurements sampled during a predetermined time interval and a set of predetermined timestamps, wherein each measurement has a corresponding timestamp. The PDA 18 includes software which algorithmically compares the measurement values to determine the two smallest values (indicative of a contracting uterus), and subtracts the lesser corresponding timestamp of the values from the greater corresponding timestamp of the measurement values to determine the time gap therebetween, indicating the length of time between uterine contractions. It should be appreciated that the software may utilize various algorithms to derive predetermined information, such as a frequency of contractions or degree of contraction.

Preferably, the processed data is displayed on the display screen 18a of the PDA 18 in a variety of useful formats, such as a line chart as shown at 60 or a bar graph of the values over a specific period of time. Advantageously, the processed data can be compared to a predetermined criterion, and a message is displayed on the display screen 18a. For example, the message may prompt the user to contact the healthcare provider as shown at 62. The user of the PDA 18 reviews the screens, redisplays selected screens, or inputs data into displayed fields by utilizing the operator control devices of the PDA 18; e.g., a stylus. As one skilled in the art will recognize, the capabilities of the PDA 18 include the functionality to process and display the information dictated by the monitoring objectives of the healthcare provider. The methodology advances to block 115.

In block 115, the processed data is transmitted by the PDA 18 to the healthcare provider via the Internet 30, as previously described. The methodology advances to block 120.

In block 120, the data is received by the healthcare provider and made available to the healthcare provider for further analysis and study. For example, the data is stored on a database on the healthcare provider's computer system 32. The information is retrieved and displayed in the form of web pages. The server stores and displays the information via web pages, either by itself or in combination with previously stored information pertinent to a particular patient profile. Further, the server utilizes various software components to process and present the information according to predetermined care objectives. It should be appreciated that the server can process data from a plurality of patients.

The healthcare provider retrieves the information via a variety of means. Typically, the server displays the information on the web pages; however, the healthcare provider may download the information from the server to a computing device of his/her choice; e.g., a PDA 36 or another personal computer (not shown).

It should be appreciated that the healthcare provider can communicate with the patient. For example, the healthcare provider, after reviewing the patient's information, uploads a text message from their computer to a common interface, such as the web site. The server of the web site transmits the information via the Internet 30 to the PDA 18, which activates an alarm to notify the patient of an incoming message, and displays the same on the display unit portion of the PDA 18.

Advantageously, the system 10 of remote pregnancy monitoring provides home-based medical care to patients in a cost-effective manner irrespective of their physical location, to enhance the health of the woman 12 and fetus 24.

Figure 4:
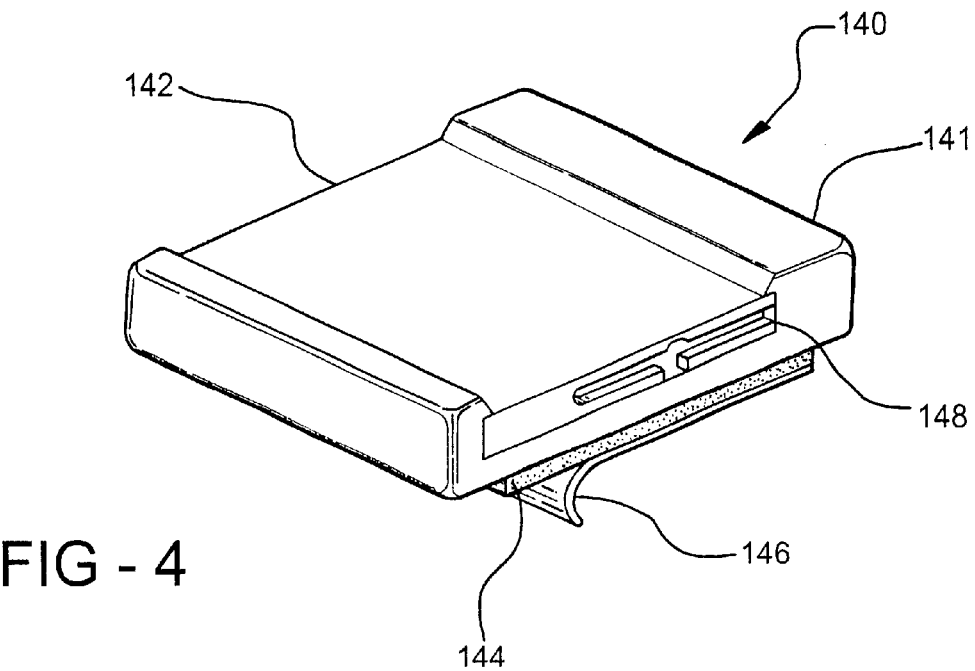
FIG. 4 is a perspective view of another embodiment of a clip for attaching the ultrasound transducer, according to the present invention.

Referring to FIG. 4, an alternative embodiment of a clip 140 for supporting the ultrasound transducer 14 and attaching the ultrasound transducer 14 to the woman's abdomen 20 is illustrated. The clip 140 includes a base 141, and a monitor housing 142 supported by the base 141. The monitor housing 142 provides a support structure for an ultrasound transducer 14, as previously described. It should be appreciated that the monitor housing 142 and ultrasound transducer 14 may be integral and one.

It should also be appreciated that the monitor housing 142 is removable from the base 141. The clip 140 also includes an adhesive layer 144, exposed by removal of a release layer 146, for adhering the clip 140 to the abdomen 20 of the woman 12. Preferably, the monitor housing 142 includes a monitor interface 148, as is known in the art, for plugging the clip 140 into an interface slot (or memory module slot) of the computer 26. This allows collected data to be transferred to the computer 26 by removing the monitor housing 142 from the clip 140 and inserting the monitor housing 142 into a suitable computer interface slot (not shown). Preferably, the monitor housing 142 encloses ultrasonic transducers, a wireless transceiver, an electrical power source, and circuitry so as to control the ultrasound transducer 14, process signals received from the ultrasound transducer 14, and send data via the communications link 16. It should be appreciated that the use of a clip 140 to support an ultrasound transducer 14 is described in more detail in co-pending provisional application No. 60/225,454, incorporated herein by reference. The clip 140 can remain adhered to the skin 160 of the woman 12, allowing improved reproducibility of transducer positioning on the abdomen 20, and providing an unobtrusive low profile with the monitor housing 142 removed from the clip 140.

Figure 5:
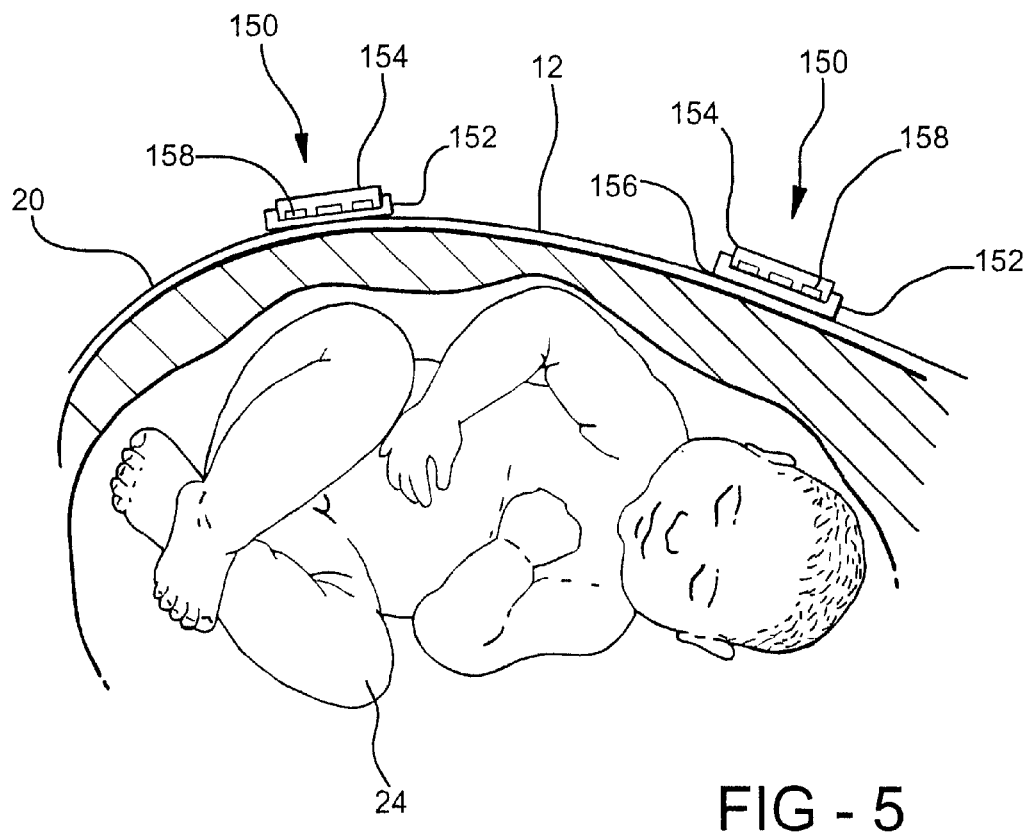
FIG. 5 is a side view of still another embodiment of a clip for attaching a plurality of ultrasound transducers, according to the present invention.

Referring to FIG. 5, still another embodiment of a clip 150 for holding a plurality of ultrasonic transducers is illustrated. The clip 150 includes a base 152 and a monitor housing 154 removably attached to the base 152 for supporting a plurality of ultrasonic transducers 158, as previously described with respect to FIG. 4. The clip 150 includes an adhesive layer 156 for securing the clip 150 to the woman 12. Preferably, the clip 150 and adhesive layer 156 includes gel-filled holes (not shown) aligned with the transducers 158, so as to provide improved acoustic coupling between the ultrasonic transducer 158 and the woman 12. Data can be transmitted from a number of such ultrasound transducers 14 to the computer 26, 30 or PDA 18 for analysis, physiological data extraction, or image processing. For example, an ultrasonic image of the fetus 24 can be formed. Advantageously, a plurality of ultrasonic transducer arrays 158 can be disposed around the abdomen 20 of the woman 12 for ultrasonic imaging, such as using phased array methods, as is known in the art.

Referring to FIG. 6, a further embodiment of a unitary monitoring device 200 for monitoring a patient, such as a pregnant woman, is illustrated. The unitary monitoring device 200 is supported on the patient, and includes a sensing mechanism 202, such as the ultrasonic transducer 203, previously described. The unitary monitoring device 200 also includes a memory 204 and a power source 206, to be described. The sensing mechanism 202 may further incorporate one or more additional physiological sensors 210, such as sensors for body temperature, metabolic rate, ion sensing, blood glucose, blood hormones, other blood components, heart rate, EKG signals, stress levels, skin conductivity, respiration frequency and depth, or the like, operative to generate electrical signals as a function of the measured physiological parameter. The sensing mechanism 202 may also include sensors for physical location, altitude, environmental parameters such as ambient temperature, and the like. Hence, the unitary monitoring device 200 is a physiological monitor, recorder and transmitter adapted to be affixed to the body of a patient. The device 160 is adapted to be employed in connection with an associated local patient computer system 26 having a display 26b and being operative to measure particular physiological parameters of the patient, store the measurements, and transmit the stored measurements to the associated computer 32 for analysis.

The electrical signals from the sensing mechanism 202, such as ultrasonic transducers 203, are converted from analog to digital form, if they are not already in that form, and then are stored in a digital memory portion 204 of the unitary monitoring device 200. The memory 204 is preferably nonvolatile, such as flash memory, but could also be volatile memory powered by the power source 206, such as the battery. The preferred form of memory 204 is of the type employed with the SONY MEMORY STICK, which constitutes flash memory in a flat physical format. An actual MEMORY STICK could be employed with a BLUETOOTH transmitter (for example, as supplied by Ericsson AB of Sweden), or transceiver and a physiological monitor associated with and plugged into the MEMORY STICK to form an integrated unit.

The unitary monitoring device 200 includes a transceiver 208 operating in the electromagnetic spectrum, such as RF or IR. The transceiver 208 preferably utilizes a widely accepted wireless transmission protocol, such as BLUETOOTH, HOMERF, IEEE 802, or IEEE 802.11, to transmit the stored signals to a computing device such as a personal digital assistant 18, patient computer system 26, or other healthcare provider computer system 32 (previously described) in communication with the transceiver 208. An example of such a monitoring system is disclosed in the inventor's co-pending U.S. patent application, Ser. No. 09/821,417, filed Mar. 29, 2001 ("Monitoring System"), incorporated herein by reference. This system may advantageously be used with ultrasonic transducers as the sensing elements. The transmissions to the computers 26, 32 may be made at regular intervals, at the end of a measurement cycle, or upon receipt of an appropriate signal by the transceiver 208 from the PDA 18.

The unitary monitoring device 200 may receive signals from other types of sensors and transducers disposed around the patient's body. For example, a plurality of ultrasonic transducers, as previously described with respect to FIG. 5, may be disposed around the patient's body, with wireless transmission of data obtained using the transducers to a single device (which may or may not contain an ultrasonic transducer), adapted to process the collected data, store the processed data, and further to transmit the processed data to a computing device. For example, imaging of the fetus 24 in two or three dimensions can be achieved using a plurality of ultrasonic transducers as previously described, disposed around the woman's abdomen 20. For example, a single ultrasonic transmitter may be used with a plurality of ultrasonic receivers. Using micromachined ultrasonic transducer arrays, transducer elements can be used as transmitters or receivers, either in a time sequential manner, based on location within the array, or based on a combination of time and spatial distributions, as is known in the art. It should be appreciated that an ultrasonic imaging module can be provided as a plug-in accessory for a PDA 18.

Preferably, the unitary monitoring device 200 is affixed to the patient's body, in an appropriate location, by a pressure sensitive adhesive, gel pad, a body-encircling strap, or similar fastening means. The unitary monitoring device 200 should be low in weight and of low profile, so as to not interfere with the patient's normal activities. The associated computing device preferably contains an application program for processing and plotting (or otherwise displaying) the signals received from the transceiver.

In this example, the unitary monitoring device 200 is used to alert a physician to the onset of labor by incorporating physiological monitors which sense the dilation of the patient's cervix or frequency and intensity of contractions, signaling the onset of labor. It should be appreciated that the ultrasonic transducers could cooperate with other transducers attached to separate portions of the patient's body, so as to measure the distance between the two transducers.

Advantageously, a physiological sensor within the unitary monitoring device 200 is used to monitor other physiological parameters related to the status of the woman 12 or fetus 24, such as measuring the body temperature of the woman 12, in which case the sensor is a thermistor or other temperature sensitive semiconductor device.

The unitary monitoring device 200 makes continuous or discrete physiological status measurements. For example, the unitary monitoring device 200 contains a clock, so that measurements are made and stored at regular intervals, such as each half hour, or when triggered by a signal sent by the associated computer 18, 26, 32. The transceiver portion of the unitary monitoring device 200 stores the output signals, and periodically transmits them to the associated computer 26, 32 or PDA 18. For example, the associated computer 26, 32 or PDA 18 processes and displays the signal in terms of the most recent data, and a plot of data over a period of time. The associated computing device 26, 32 or PDA 18 includes a display allowing the user or others to review the displayed data.

The associated computing device 26, 32 or PDA 18 preferably includes a communication link 28, as previously described, for sending the accumulated information over a public network such as the Internet 30 to a remote site which could constitute a website associated with the healthcare provider and available to a remotely located healthcare provider through an appropriate terminal. In this manner, the healthcare provider could periodically review the plot of the patient's and fetus's status as well as other physiological data contained in the website in order to develop treatment instructions. These instructions could be transmitted by the healthcare provider over the public network 30 to the patient's computer 26 for display to the patient. Thus, after reviewing the patient's data, the healthcare professional might transmit a message, such as "take medication" or, alternatively, "go immediately to the hospital."

It is contemplated that the website may include software for reviewing the measured parameters and sending alert signals to the healthcare provider when the parameters meet certain preset conditions. In this example of a pregnant patient, the website could send an alert signal to the attending physician whenever the measured contraction period and/or strength of contractions are indicative of imminent delivery of the fetus 24.

Alternatively, the unitary monitoring device 200 includes a sensing mechanism 202 for generating signals representative of the patient's body movement. For example, information relating to the patient's body activity and caloric consumption, such as for blood sugar control during pregnancy, is available. In this example, the sensing mechanism is a 2D or 3D accelerometer.

In another example of the use of the unitary monitoring device 200, the sensing mechanism 202 is an ultrasonic transducer attached to a separated portion of the body to measure posture, either for a posture correcting system or to detect an abnormality of posture associated with a particular disorder.

In still another example of the use of the unitary monitoring device 200, the sensing mechanism 202 incorporates a sub-dermal transducer to measure the characteristics of body fluids, such as blood for blood hormone or blood sugar monitoring. Interstitial fluid can be monitored for glucose, hormones, and the like using sensors below the epidermis. The unitary monitoring device 200 itself would be attached to the outer body, but the sensor would include a needle-like probe which extends below the skin surface to contact the desired body fluids. One or more microneedles can be used to extract interstitial fluid for analysis. In addition, the probe may incorporate an ion selective transducer for measurement of blood glucose or the like.

It should be appreciated that the unitary monitoring device 200 of the present invention can cooperate with a hand-held computer or PDA 18 which is used to accumulate a variety of physiological information. For example, a patient uses the keyboard of the PDA 18 to enter information relating to food, beverage, and medication consumption, or other physiological or psychological parameters. In another example, the patient uses a scale, which incorporates a transmitter, such as a Bluetooth™ transmitter, to send weight information to the associated computer 26, 30. In still another example, the patient employs an indirect calorimeter to measure the patient's metabolism. This information could be plotted using the associated personal digital assistant 18 or PC 26 and made available to the healthcare provider's computer 32 via the internet 30 or other public network. From this information, a healthcare provider can make an accurate evaluation of the patient's health and physiological status, as well as that of a fetus 24, if fetus 24 physiological data is available, and communicate comments and instructions back to the patient for viewing on the patient's PDA 18.

Advantageously, the present invention closes the existing physical separation between a physician and patients. A physician is in a position to constantly monitor a patient's status or monitor it in accordance with the physician's discretion rather than waiting for a patient to make a visit to the physician. A computer expert system, resident on a computer receiving data from sensors on the body of a patient, can also be used to generate warnings, alerts, and advice to the patient.

The present invention has been described in an illustrative manner. It is to be understood that the terminology, which has been used, is intended to be in the nature of words of description rather than of limitation.

Many modifications and variations of the present invention are possible in light of the above teachings. Therefore, within the scope of the appended claims, the present invention may be practiced other than as specifically described.

What is claimed is:

1. A system for remote pregnancy monitoring of a pregnant woman comprising:
   an ultrasound transducer having a processor, a transmitter and a receiver, wherein said transducer is positioned on a pregnant woman;
   a personal digital assistant operatively connected to said ultrasound transducer via a communication link;
   a patient computer system operatively connected to said personal digital assistant via a second communication link, wherein said patient computer system includes a memory, a processor, a display device and an input device; and
   a healthcare provider computer system operatively connected to said patient computer system via an internet, wherein said healthcare provider computer system includes a memory, a processor, a display device and an input device, and activation of said ultrasound transducer generates a data signal that is transmitted to said personal digital assistant via said communication link, and transmission of said signal to said healthcare provider computer system via said second communication link, for monitoring the pregnant woman by a healthcare provider.

2. A system as set forth in claim 1 wherein said ultrasound transducer is an ultrasonic transducer having a plurality of microscopic transducers arranged in an array on a silicon wafer.

3. A system as set forth in claim 1 wherein said PDA includes a memory, a processor, a display screen and an input mechanism.

4. A system as set forth in claim 1 wherein said communication link is a wireless communication link.

5. A system as set forth in claim 1 wherein an internet is the Internet.

6. A system as set forth in claim 1 wherein said healthcare provider computer system is operatively connected to a plurality of patient computer systems, for monitoring a plurality of pregnant women.

7. A system for remote pregnancy monitoring of a pregnant woman comprising:
   an ultrasound transducer having a processor, a transmitter and a receiver, wherein said transducer is positioned on a pregnant woman;
   a personal digital assistant operatively connected to said ultrasound transducer via a communication link, wherein said personal digital assistant includes a memory, a processor, a display screen, an input mechanism, and a wireless communication mechanism for wireless communication via the internet;
   a healthcare provider computer system in communication with said personal digital assistant via the internet, wherein said healthcare provider computer system includes a memory, a processor, a display device and an input device; and
   activation of said ultrasound transducer generates transmission of a data signal to said personal digital assistant via said communication link, and wireless transmission of said signal between said personal digital assistant and said healthcare provider computer system over the internet for analysis by the healthcare provider.

8. A system as set forth in claim 7 wherein said ultrasound transducer is an ultrasonic transducer having a plurality of microscopic transducers arranged in an array on a silicon wafer.

9. A system as set forth in claim 7 wherein said communication link is a wireless communication link.

10. A system as set forth in claim 7 wherein an internet is the Internet.

11. A system as set forth in claim 7 wherein said healthcare provider computer system is operatively connected to a plurality of patient computer systems for monitoring a plurality of pregnant women.

12. A method for remote pregnancy monitoring of a pregnant female, said method comprising the steps of:
   positioning an ultrasound transducer on the pregnant female in a predetermined location to monitor a predetermined condition;
   activating the ultrasound transducer to generate a signal for monitoring the predetermined condition, wherein the ultrasound transducer includes a processor, a transmitter and a receiver;
   transmitting the signal from the ultrasound transducer to a personal digital assistant, wherein the personal digital assistant includes a memory, a processor, a display screen and an input mechanism;
   transmitting the signal for monitoring the predetermined condition from the personal digital assistant via an internet to a healthcare provider computer, wherein the healthcare provider computer includes a memory, a processor, a display screen and an input device; and
   using the signal to remotely monitor the pregnant woman.

13. A method as set forth in claim 12 wherein said ultrasound transducer is an ultrasonic transducer having a plurality of microscopic transducers arranged in an array on a silicon wafer.

14. A method as set forth in claim 12 wherein said step of transmitting the signal between the ultrasound transducer and the personal digital assistant includes transmitting the signal via a wireless communication link.

15. A method as set forth in claim 12 wherein said step of transmitting the signal from the personal digital assistant includes the step of transmitting the signal via the Internet.

16. A method as set forth in claim 12 wherein said step of transmitting the signal from the personal digital assistant includes the step of transmitting the signal to a patient computer system having a memory, a processor, a display screen, and an input device.

17. A system as set forth in claim 12 including the step of receiving, by said healthcare provider computer system, a plurality of signals from a plurality of pregnant women, for monitoring a plurality of pregnant women.

18. A system for remote pregnancy monitoring of a pregnant woman comprising:
    an ultrasound transducer having a processor, a transmitter and a receiver;
    a clip for attaching said ultrasound transducer to the pregnant woman, wherein said clip includes a base, a monitor housing for the ultrasound transducer supported by said base, and an adhesive layer for adhering said clip to the woman;
    a personal digital assistant operatively connected to said clip via a communication link;
    a patient computer system operatively connected to said personal digital assistant via a second communication link, wherein said patient computer system includes a memory, a processor, a display device and an input device; and
    a healthcare provider computer system operatively connected to said patient computer system via an internet, wherein said healthcare provider computer system includes a memory, a processor, a display device and an input device, and activation of said ultrasound transducer generates a data signal that is transmitted to said personal digital assistant via said communication link, and transmission of said signal to said healthcare provider computer system via said second communication link, for monitoring the pregnant woman by a healthcare provider.

19. A system as set forth in claim 18 wherein said clip includes a plurality of ultrasound transducers disposed therein.

20. A system for remote pregnancy monitoring of a pregnant woman comprising:
    a unitary monitoring device, wherein said unitary monitoring device includes a sensing mechanism, a memory, a power source, a transmitter, and a processor;
    a personal digital assistant operatively connected to said unitary monitoring device via a communication link;
    a patient computer system operatively connected to said personal digital assistant via a second communication link, wherein said patient computer system includes a memory, a processor, a display device and an input device; and
    a healthcare provider computer system operatively connected to said patient computer system via an internet, wherein said healthcare provider computer system includes a memory, a processor, a display device and an input device, and activation of said unitary monitoring device generates a data signal that is transmitted to said personal digital assistant via said communication link, and transmission of said signal to said healthcare provider computer system via said second communication link, for monitoring the pregnant woman by a healthcare provider.

21. A system as set forth in claim 20 wherein said sensing mechanism is an ultrasound transducer.

* * * * *